(12) United States Patent
Ullah

(10) Patent No.: US 9,073,900 B2
(45) Date of Patent: Jul. 7, 2015

(54) DIHYDROQUINONE DERIVATIVES OF PIPERIDINE AND PIPERAZINE

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventor: Nisar Ullah, Dhahran (SA)

(73) Assignees: KING FAHD UNIVERSITY OF PETROLEUM AND MINERALS, Dhahran (SA); KING ABDULAZIZ CITY FOR SCIENCE AND TECHNOLOGY, Riyadh (SA)

( * ) Notice: Subject to any disclaimer, the term of this patent is extended or adjusted under 35 U.S.C. 154(b) by 0 days.

(21) Appl. No.: 14/543,348

(22) Filed: Nov. 17, 2014

(65) Prior Publication Data

US 2015/0094467 A1    Apr. 2, 2015

Related U.S. Application Data

(62) Division of application No. 14/044,826, filed on Oct. 2, 2013, now Pat. No. 8,916,704.

(51) Int. Cl.
*C07D 239/80*    (2006.01)
*C07D 401/12*    (2006.01)

(52) U.S. Cl.
CPC ............ *C07D 401/12* (2013.01); *C07D 239/80* (2013.01)

(58) Field of Classification Search
CPC .................................................. C07D 239/80
See application file for complete search history.

(56) References Cited

U.S. PATENT DOCUMENTS 7,053,098 B1    5/2006  Adams et al.

OTHER PUBLICATIONS

Hasegawa, et al., A novel class of sodium/calcium exchanger inhibitor: design, synthesis, and structure-activity relationships of 3,4-dihydro-2(1H)-quinazolinone derivatives, Bioorganic & Medicinal Chemistry 13, 3721-3735 (2005).*
H. Hasegawa et al., "A Novel Class of Sodium/Calcium Exchanger Inhibitor: Design, Synthesis, and Structure-Activity Relationships of 3,4-Dihydro-2(1H)-quinazolinone Derivatives", Bioorganic & Medicinal Chemistry (Jun. 2005), vol. 13, Iss. 11, pp. 3721-3735.
R.M. Rzasa et al., "Structure-Activity Relationships of 3,4-Dihydro-1H-quinazolin-2-one Derivatives as Potential CDK5 Inhibitors", Bioorganic & Medicinal Chemistry (Oct. 2007), vol. 15, Iss. 20, pp. 6574-6595.
N. Ullah, "Synthesis of new 1-Aryl-4-(biarylmethylene)piperazine ligands, structurally related to adoprazine (SLV313)", Z Naturforsch (2012) vol. 67b, pp. 75-84.
N. Ullah et al., "Synthesis of new 4-aryl-1-(biarylmethylene)piperidines: Structural analogs of adoprazine (SLV313)", Z Naturforsch (2012) vol. 67b, pp. 253-262.
NPL have been properly filed in parent U.S. Appl. No. 14/044,826, filed Oct. 2, 2013, priority of which is claimed.

* cited by examiner

*Primary Examiner* — Erich A Leeser
(74) *Attorney, Agent, or Firm* — Richard C Litman

(57) ABSTRACT

The dihydroquinone derivatives of piperidine and piperazine are 7-piperazinyl and 7-piperadinyl-3,4-dihydroquinazolin-2(1H)-ones that exhibit $D_2$ and 5-$HT_{1A}$ receptor binding affinities, making them suitable for use as the active ingredient of pharmaceuticals for the treatment of schizophrenia. The derivatives have the general formula:

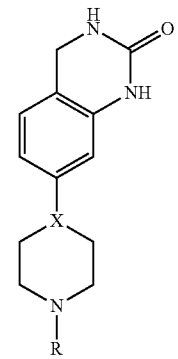

where X is carbon or nitrogen and R is a group selected from a through f having the formula:

a b c

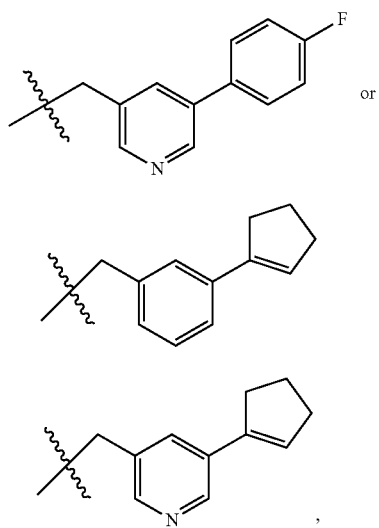

or a pharmaceutically acceptable salt thereof. The piperazine compounds are prepared by condensing 4-bromo-2-nitrobenzonitrile with 1-Boc-piperazine (1-tert-butoxycarbonyl-piperazine) to form an intermediate that is converted to a piperazinyl-3,4-dihydroquinazolin-2(1H)-one. Subsequent reductive amination with the biarylaldehydes a through f completes the synthesis of the 7-piperadinyl-3,4-dihydroquinazolin-2(1H)-ones. The piperadinyl compounds are prepared from tert-butyl-4-(2-oxo-1,2,3,4-tetradihydroquinazolin-7-yl)piperidine-1-carboxylate, which is converted to 7-(piperidin-4-yl)-3,4-dihyroquinazolin-2(1H)-one. Subsequent reductive amination with the biarylaldehydes a through f completes the synthesis of the 7-piperidinyl-3,4-dihydroquinazolin-2(1H)-ones.

8 Claims, 4 Drawing Sheets

DIHYDROQUINONE DERIVATIVES OF PIPERIDINE AND PIPERAZINE

CROSS-REFERENCE TO RELATED APPLICATIONS

This is a division of my prior application Ser. No. 14/044,826, filed Oct. 2, 2014, now pending.

BACKGROUND OF THE INVENTION

1. Field of the Invention

The present invention relates to pharmaceuticals, and particularly to dihydroquinone derivatives of piperidine and piperazine useful for the treatment of schizophrenia.

2. Description of the Related Art

Schizophrenia is a devastating psychiatric illness afflicting 1% of the population worldwide. The diagnosis of disease is based on diverse and variably expressed symptoms that can be grouped as positive and negative. The positive symptoms include disorganized thought, delusions, and auditory hallucinations while negative symptoms are emotional flattening, poverty of speech and motivational deficits. The first-generation antipsychotics, such as chlorpromazine 1 and haloperidol 2a, are dopamine antagonists and exhibit robust control of positive symptoms, such as hallucinations, agitation and delusions, but fail to control the negative symptoms, for instance, blunted affect, emotional withdrawal and cognitive deficits.

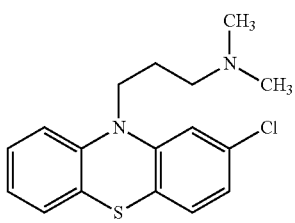

1

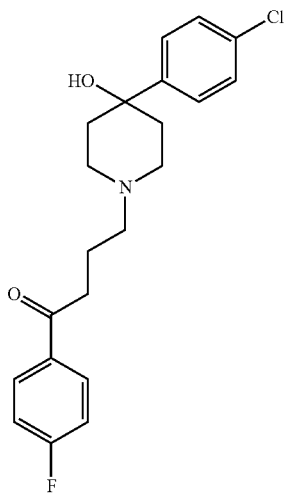

2a

In addition, selective $D_2$ receptor antagonists lead to extrapyramidal symptoms (EPS), such as dystonia and dyskinesia, and hyperprolactinemia. With respect to classical neuroleptics, the 'second-generation' or atypical antipsychotics, such as clozapine 2b, show significantly greater efficacy, including an improved effect on negative symptoms, and causes a marked increase in dopamine output in the prefrontal cortex

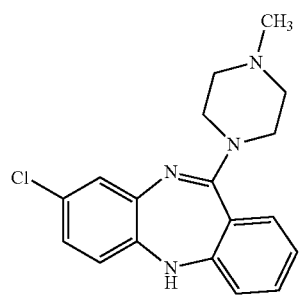

2b

Clozapine 2b exhibits partial agonist efficacy for $5\text{-}HT_{1A}$ receptor-mediated stimulation of G-protein activation, which accounts for part of the activity of clozapine in a model of anxiolytic-like activity, namely, clozapine inhibited stress-induced ultrasonic vocalization in rats, an effect attenuated by selective $5\text{-}HT_{1A}$ antagonist WAY-100635. With respect to first generation antipsychotics, clozapine 2b shows significantly greater efficacy, including an improved effect on negative symptoms, and causes a marked increase in dopamine output in the prefrontal cortex. However, clozapine is implicated in a set of serious side effects, such as weight gain, diabetes and an increased risk of seizures and agranulocytosis.

Although the utility of $5\text{-}HT_{1A}$ receptor agonism in the treatment of schizophrenia is clearly evident, the optimal level of activation of this target is debatable. To achieve improved overall therapeutic benefit, combining $D_2$ receptor antagonism with $5\text{-}HT_{1A}$ receptor agonism, rather than antagonism, has attracted a great deal of interest recently. Several mechanistic considerations and preclinical evidence have supported the potential of such a combination. As a result, adoprazine 3 (SLV-313) and bifeprunox 4, which are potent $D_2$ receptor antagonists and $5\text{-}HT_{1A}$ receptor agonists, were developed.

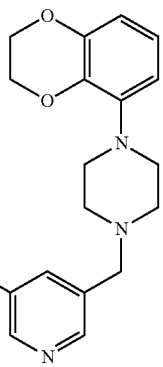
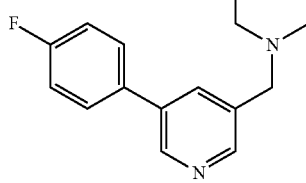

3

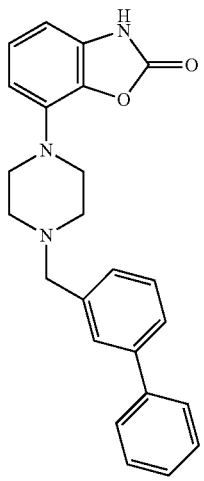

The antipsychotic efficacy of bifeprunox 4 was determined to be inferior to that of risperidone and olanzapine, and despite a satisfactory tolerance profile, the FDA did not grant marketing approval. The lack of sufficient antipsychotic efficacy of bifeprunox 4 likely reflects its marked agonism at $D_2$ receptors. Thus, bifeprunox 4 suppresses basal firing rates of dopaminergic neurons in the ventral tegmental area and elicits circling behavior in rats unilaterally lesioned with 6-OH-DA. In addition, the failure of adoprazine 3 and bifeprunox 4 to oppose phencyclidine-induced social interaction deficits suggested that an appropriate 'balance' of activity at these sites is necessary for activity in this model. Therefore, there is a need to discover new chemical entities bearing varying ratios of $D_2$ and 5-$HT_{1A}$ activities.

Thus, dihydroquinone derivatives of piperidine and piperazine solving the aforementioned problems are desired.

SUMMARY OF THE INVENTION

The dihydroquinone derivatives of piperidine and piperazine are 7-piperazinyl and 7-piperadinyl-3,4-dihydroquinazolin-2(1H)-ones that exhibit $D_2$ and 5-$HT_{1A}$ receptor binding affinities, making them suitable for use as the active ingredient of pharmaceuticals for the treatment of schizophrenia. The derivatives have the general formula:

where X is carbon or nitrogen and R is a group selected from a through f having the formula:

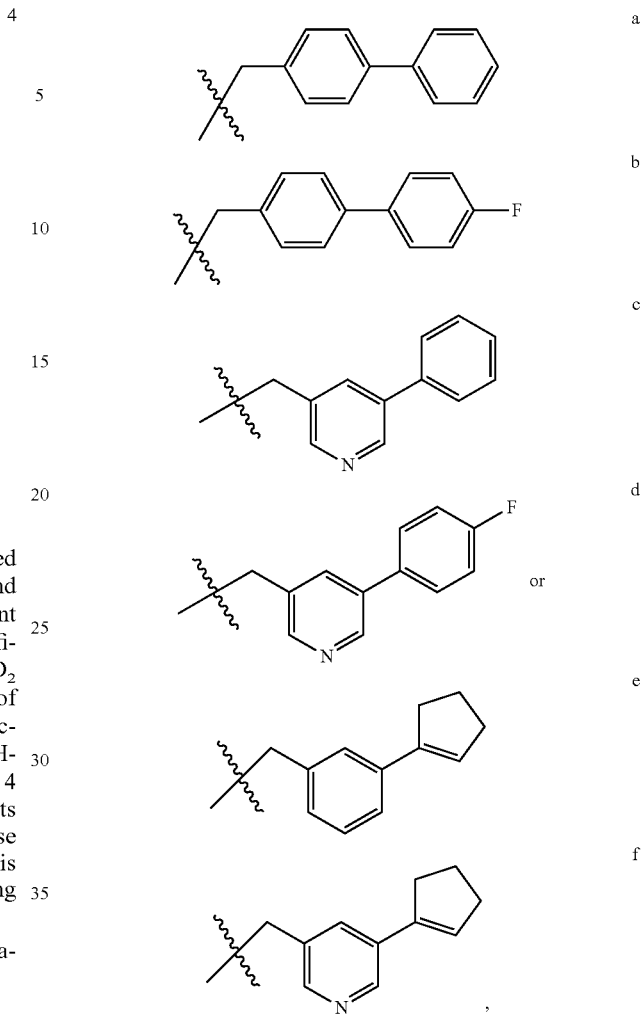

or a pharmaceutically acceptable salt thereof. The piperazine compounds are prepared by condensing 4-bromo-2-nitrobenzonitrile with 1-Boc-piperazine (1-tert-butoxycarbonyl-piperazine) to form an intermediate that is converted to a piperazinyl-3,4-dihydroquinazolin-2(1H)-one. Subsequent reductive amination with the biarylaldehydes a through f completes the synthesis of the 7-piperazinyl-3,4-dihydroquinazolin-2(1H)-ones. The piperadinyl compounds are prepared from tert-butyl-4-(2-oxo-1,2,3,4-tetradihydroquinazolin-7-yl)piperidine-1-carboxylate, which is converted to 7-(piperidin-4-yl)-3,4-dihyroquinazolin-2(1H)-one. Subsequent reductive amination with the biarylaldehydes a through f completes the synthesis of the 7-piperidinyl-3,4-dihydroquinazolin-2(1H)-ones.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The dihydroquinone derivatives of piperidine and piperazine are 7-piperazinyl and 7-piperadinyl-3,4-dihydroquinazolin-2(1H)-ones that exhibit $D_2$ and 5-$HT_{1A}$ receptor binding affinities, making them suitable for use as the active ingredient of pharmaceuticals for the treatment of schizophrenia. The derivatives have the general formula:

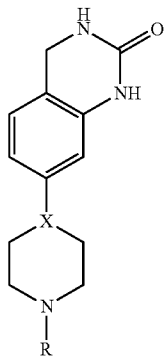

where X is carbon or nitrogen and R is a group selected from a through f having the formula:

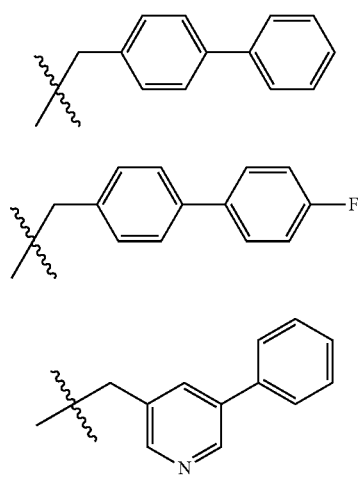

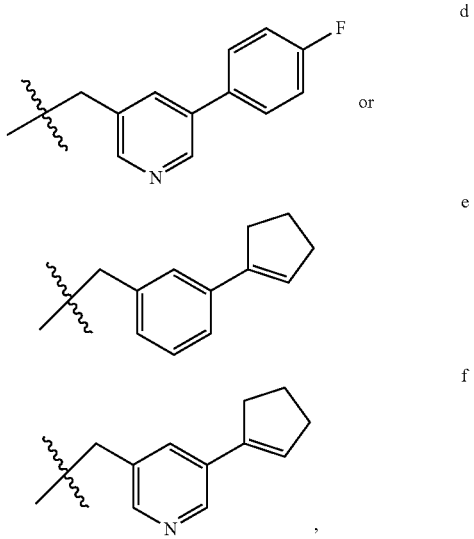

or a pharmaceutically acceptable salt thereof. The piperazine compounds are prepared by condensing 4-bromo-2-nitrobenzonitrile with 1-Boc-piperazine (1-tert-butoxycarbonyl-piperazine) to form an intermediate that is converted to a piperazinyl-3,4-dihydroquinazolin-2(1H)-one. Subsequent reductive amination with the biarylaldehydes a through f completes the synthesis of the 7-piperazinyl-3,4-dihydroquinazolin-2(1H)-ones. The piperadinyl compounds are prepared from tert-butyl-4-(2-oxo-1,2,3,4-tetradihydroquinazolin-7-yl)piperidine-1-carboxylate, which is converted to 7-(piperidin-4-yl)-3,4-dihyroquinazolin-2(1H)-one. Subsequent reductive amination with the biarylaldehydes a through f completes the synthesis of the 7-piperidinyl-3,4-dihydroquinazolin-2(1H)-ones.

Figure 1:
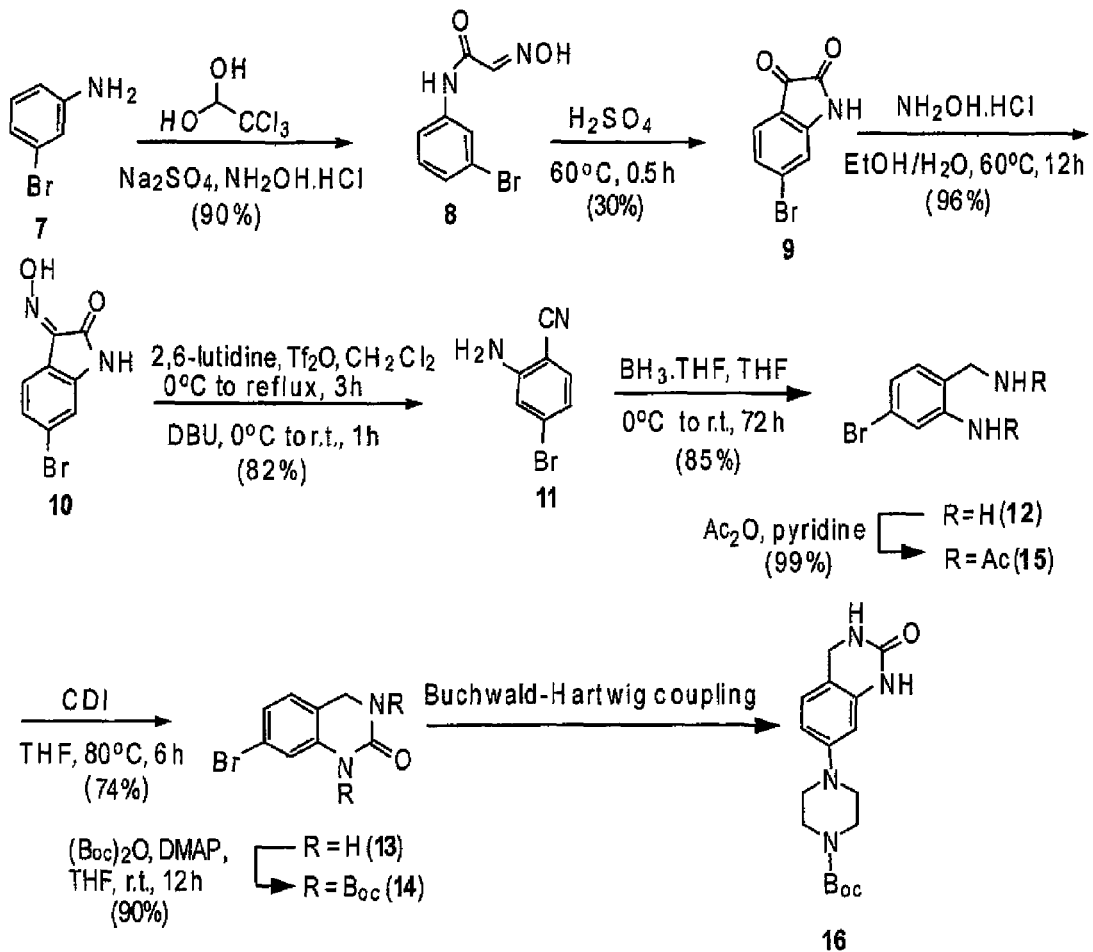
FIG. 1 is a proposed reaction scheme for the synthesis of an intermediate compound, namely, tert-Butyl 4-(2-oxo-1,2,3,4-tetrahydroquinazolin-7-yl)piperazine-1-carboxylate, which is used in the synthesis of the dihydroquinone derivatives of piperazine according to the present invention.

Referring to FIG. 1, the synthesis of piperazinyl compounds 5a-5f required the key intermediate 16, which was envisioned to be synthesized by Buchwald-Hartwig reaction of bromo-3,4-dihydroquinazolin-2(1H)-one 13 with tert-butyl piperazine-1-carboxylate. Therefore, preparation of 13 was commenced with the reaction of bromoaniline 7 with chloral hydrate and hydroxylamine hydrochloride to afford the corresponding isonitrosoacetanilide 8, which, in turn, was heated in concentrated sulfuric acid to afford (after regioisomers separations) isatin 9. Condensation of intermediate 9 with hydroxylamine hydrochloride smoothly furnished oxime 10. Intermediate 10 was treated with trifluorosulfonic anhydride, followed by exposure of the resultant trifluorate to DBU to afford nitrile 11 in 82% yield. Reduction of intermediate 11 with borane at room temperature generated diamine 12 in good yield 85%. Reaction of diamine 12 with carbonyldiimidazole CDI in THF at 80° C. finally furnished intermediate 13 in 74% yield. However, unexpectedly, the Buchwald-Hartwig coupling of bromide 13 with tert-butyl piperazine-1-carboxylate under different reaction conditions, such as $PdCl_2$ dppf, KOAc, DMF, 80° C.; and $Pd(PPh_3)_4$, toluene, ethanol, $Na_2CO_3$, reflux, were unsuccessful. The desired intermediate 16 was not observed in any case. Rather, the starting intermediate 13 was recovered instead (scheme 1). Therefore, bromide 13 was protected with di-tert-butyl dicarbonate to furnish 14, whereas diamine 12 was acetylated with acetic anhydride in pyridine to render intermediate 15. Buchwald-Hartwig reaction of intermediates 14 or 15 with tert-butyl piperazine-1-carboxylate under different reaction conditions, as was attempted in the case of intermediate 13, also failed. The desired coupled products were not detected in any case. Rather, the starting 13 (when 14 was used as coupling partner) and 15 were recovered from the reactions instead (see FIG. 1).

Figure 2:
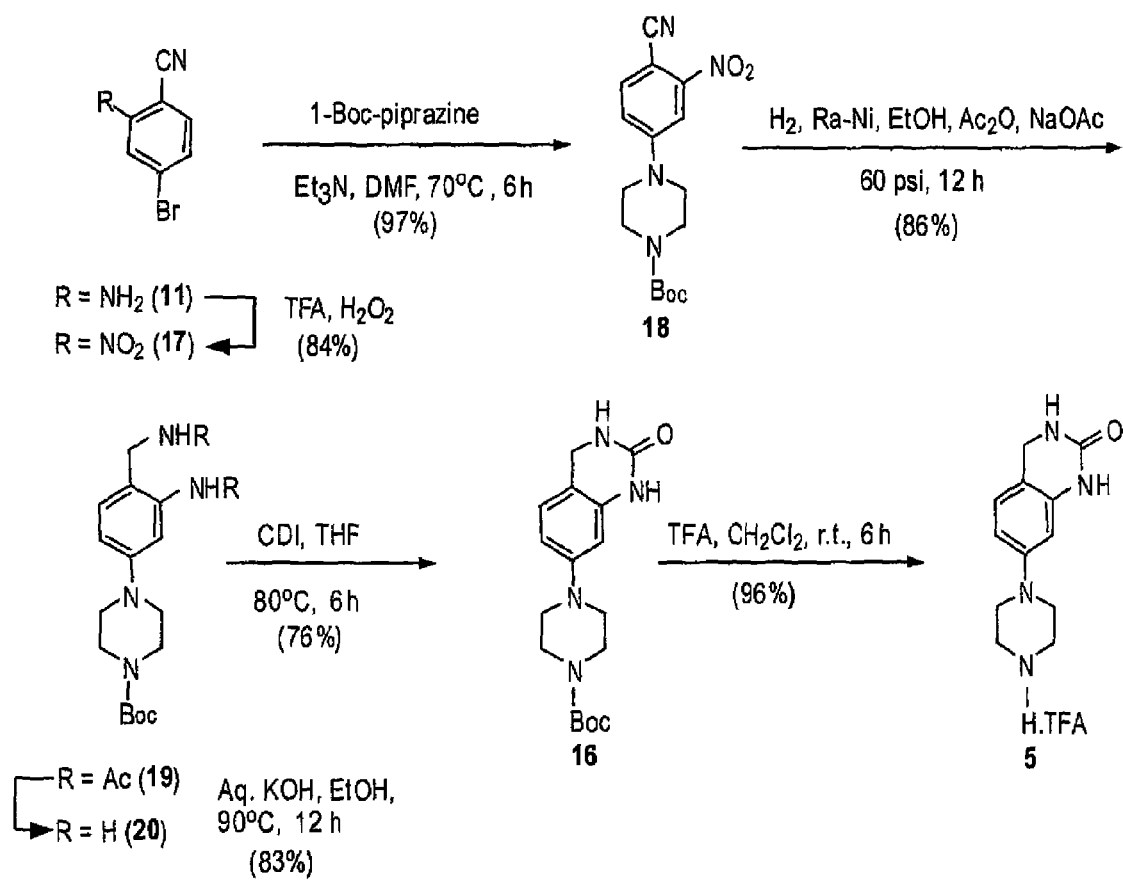
FIG. 2 is an alternative reaction scheme for the synthesis of the intermediate compound, tert-Butyl 4-(2-oxo-1,2,3,4-tetrahydroquinazolin-7-yl)piperazine-1-carboxylate, which is used in the synthesis of the dihydroquinone derivatives of piperazine according to the present invention.

Referring to FIG. 2, in an alternate approach, the amino group of nitrile 11 was oxidized with $CF_3CO_3H$ to afford nitrobenzonitrile 17, which, in turn, was heated with tert-butyl piperazine-1-carboxylate to obtain intermediate 18 in high yield (97%). It is worth mentioning that the reaction of nitrile 11 with tert-butyl piperazine-1-carboxylate, even at elevated temperature, did not yield any substituted product. The starting compound 11 remained intact. To reduce the nitrile and nitro groups of intermediate 18, it was subjected to hydrogenation over Ra—Ni in a Parr apparatus at 60 psi for 12 h. The reaction was sluggish, and hence produced the desired diamine 20 in a very low yield (16%) after column purifications. It is well established that the reduction of nitrile proceeds stepwise through the aldimine, some of which condenses with primary amine already formed and ultimately leads to secondary amines. Therefore, hydrogenation of 18 over Ra—Ni was repeated with the addition of acetic anhydride (6 equivalents) and sodium acetate (4 equivalents) in the Parr apparatus at 60 psi for 12 h, which resulted in the reduction of both nitrile and nitro groups with concomitant acetylation, yielding intermediate 19 in 86% yield. Basic hydrolysis of intermediate 19 with aqueous KOH in ethanol ultimately generated diamine 20 in an overall yield of 71% from 18. Reaction of intermediate 20 with CDI in THF, heating the mixture at 80° C. for 6 hours, afforded access to the key intermediate 16. Exposure of compound 16 to trifluoroacetic acid in dichloromethane finally furnished the desired key intermediate 5 in 96% yield (see FIG. 2).

Figure 3:
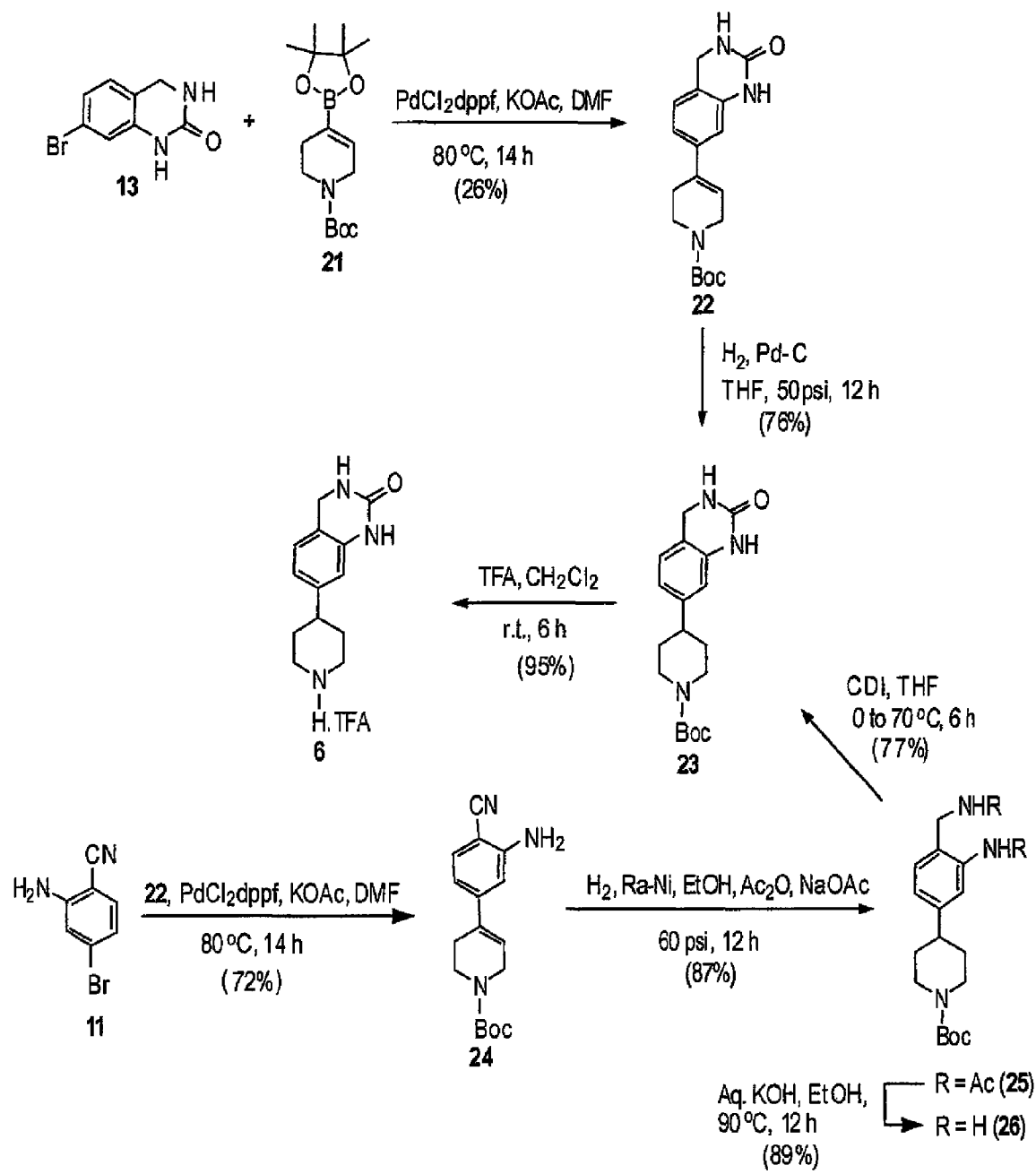
FIG. 3 is a reaction scheme for the synthesis of an intermediate compound, namely, 7-(piperidin-4-yl)-3,4-dihydroquinazolin-2(1H)-one, which is used in the synthesis of the dihydroquinone derivatives of piperidine according to the present invention.

Referring to FIG. 3, the synthesis of piperidinyl compounds 6a-6f required the synthesis of intermediate 6. The Suzuki-Miyaura reaction of intermediate 13 with boronate 21 was carried out in a mixture of toluene and ethanol, using $Pd(PPh_3)_4$ as catalyst, which afforded the desired intermediate 22 in a very low yield (12%). Therefore, the Suzuki reaction was repeated in DMF at 80° C., using $PdCl_2$-dppf as catalyst and KOAc as a base to furnish compound 22 in a slightly improved yield of 26%. The reduction of the double bond of 22 was accomplished by hydrogenation in a Parr apparatus over Pd—C at 60 psi for 12 h to produce the advanced intermediate 23 in 20% overall yield from intermediate 13. Alternatively, intermediate 23 was also synthesized from Suzuki reaction of nitrile 11 with boronate 21 to render the coupled adduct 24, which, in turn, was hydrogenated over Ra—Ni at 60 psi in the presence of acetic anhydride (6 equivalents) and sodium acetate (4 equivalents) to afford intermediate 25 in an overall yield of 62% from intermediate 11.

Removal of the acetyl groups with aqueous KOH in ethanol ultimately generated diamine 26, which, in turn, was reacted with CDI in THF to furnish intermediate 23. This alternate route produced intermediate 23 from 11 in an overall yield of 43%. Exposure of intermediate 23 to trifluoroacetic acid in dichloromethane finally furnished the desired key intermediate 6 in 94% yield.

Figure 4:
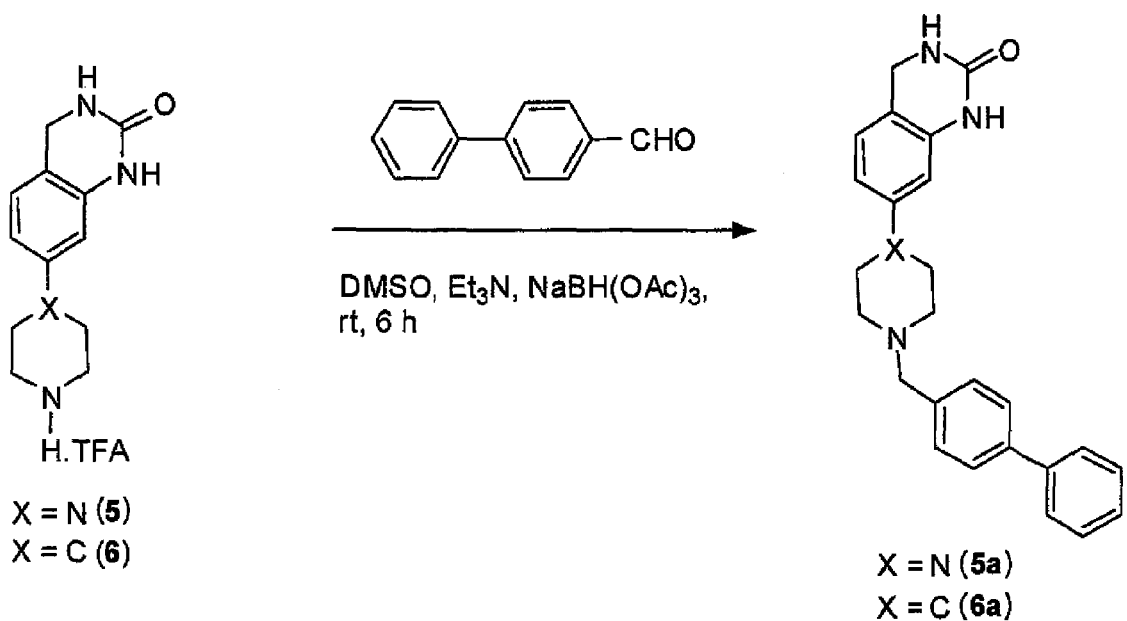
FIG. 4 is a reaction scheme for the synthesis of the biphenyl-methyl dihydroquinone derivatives of piperazine and pipridine according to the present invention.

Referring to FIG. 4, having the desired intermediates 5 and 6 in hand, we next performed reductive amination of 5 and 6 with aldehydes a-f in DMSO, using $NaBH(OAc)_3$ as reducing agent to accomplish the synthesis of final compounds (5a-f) and (6a-f), respectively.

Details of the synthesis of the various compounds shown in FIGS. 1-4 are described in the following examples. Melting Points were determined on a Büchi apparatus and are uncorrected. Elemental analysis was carried out on a Perkin Elmer Elemental Analyzer Series 11 Model 2400. IR spectra were recorded on a Perkin Elmer 16F PC FTIR spectrophotometer. The $^1H$ and $^{13}C$ NMR spectra were measured in $CDCl_3$ and $d_6$-DMSO using TMS as internal standard on a JEOL LA 500 MHz spectrometer. Mass spectra were recorded on a GC-MS system (Agilent Technologies, 6890 N). Analytical TLC was carried out on silica gel 60 $F_{254}$ plates. Column chromatography was carried out on Merck silica gel (200-400 mesh).

Example 1

Synthesis of 6-Bromo-3-(hydroxyimino)indolin-2-one 10

To a solution of compound 9 (10 g, 44.44 mmol) in EtOH (130 mL) was added a solution of hydroxylamine hydrochloride (4.61 g, 66.37 mmol) in $H_2O$ (20 mL), and the mixture was stirred at 80° C. for 12 h. The mixture was concentrated under reduced pressure and the solid formed was filtered, washed with cold water, and dried under high vacuum to afford 10.24 g (96%) of compound 10 as a blood-red solid. IR (KBr) vmax. $cm^{-1}$: 3336, 3330 ($NH_2$), 3310 (OH), 3038 (Ar—H), 2920 (Alph-H), 1690 (C=O), 1612, 1515, 1414 (C=C), 1260 (C—N). $^1H$ NMR (500 MHz, DMSO-$d_6$) δ=7.02 (s, 1H, H-7); 7.20 (d, 1H, J=8.2 Hz, H-5); 7.84 (d, 1H, J=8.1 Hz, H-4); 10.83 (s, 1H, NH); 13.49 (s, 1H, OH); $^{13}C$ NMR (125.7 MHz, DMSO-$d_6$) δ=113.12 (aromatic-C), 115.50 (aromatic-C), 124.84 (aromatic-C), 128.46 (aromatic-C), 143.48 (aromatic-C), 144.02 (aromatic-C), 164.29, 167.12 (C=O). Calculated (%) for $C_8H_5BrN_2O_2$ (239.95); C: 39.86, H: 2.09, N: 11.62. found (%); C: 39.80, H: 2.14, N: 11.58.

Example 2

Synthesis of 2-Amino-4-bromobenzonitrile 11

To a cold solution of oxime (10) (8 g, 33.33 mmol) in $CH_2Cl_2$ (200 mL) at 0° C. was added 2,6-lutidine (4.5 mL, 38.7 mmol), followed by the dropwise addition of triflouromethanesulfonic anhydride (5.6 mL, 33.33 mmol). The cooling bath was removed, and the mixture was heated to reflux for 3 h. The reaction mixture was cooled to room temperature, and DBU (9.9 mL, 66.66 mmol) was added dropwise while maintaining the internal temperature of the reaction below 30° C. The mixture was further stirred at room temperature for 1 h and poured with vigorous stirring into excess dilute $NaHCO_3$. This mixture was then stirred for several minutes, and the organic layer was separated. The aqueous layer was re-extracted with $CH_2Cl_2$ (100 mL×2). The combined extracts were dried with $MgSO_4$ and concentrated to leave a dark brown solid, which was passed through a short silica column, eluting with $CH_2Cl_2$ (100%). The resulting fraction was dried under vacuum, triturated with $CH_2Cl_2$/hexanes, and the solid formed was filtered and dried under vacuum to afford 5.36 g (82%) of 11 as a light yellow solid. IR (KBr) vmax. $cm^{-1}$: 3436, 3310 ($NH_2$), 3032 (Ar—H), 2920 (Alph-H), 2246 (CN), 1610, 1512, 1418 (C=C). $^1H$ NMR (500 MHz, $CDCl_3$) δ=4.47 (br. s, 2H, $NH_2$); 6.88 (dd, 1H, J=2.8, 8.2 Hz, H-5); 6.94 (br. s, 1H, H-3); 7.24 (d, 1H, J=8.2 Hz, H-6); $^{13}C$ NMR (125.7 MHz, $CDCl_3$) δ=95.17 (C-1), 117.16 (CN), 118.15 (C-3), 121.60 (C-5), 129.03 (C-4), 133.60 (C-6), 150.47 (C-2). Calculated (%) for $C_7H_5BrN_2$ (195.96); C: 42.67, H: 2.56, N: 14.22. found (%); C: 42.60, H: 2.61, N: 14.17.

Example 3

Synthesis of 2-(Aminomethyl)-5-bromoaniline 12

To a solution of compound (11) (2 g, 10.0 mmol) in dry THF at 0° C. under an argon atmosphere was slowly added borane (15 mL, 1.0 M in THF). The reaction mixture was stirred for 10 min at 0° C. and further 72 h at room temperature. The reaction mixture was cooled to 0° C. and quenched by addition of ethanol (96%). The resulting suspension was extracted with ethyl acetate (3×20 mL). The combined organic layers were dried over sodium sulfate. Ethyl acetate was completely removed under reduced pressure and the residues were chromatographed over silica column, eluting with ethyl acetate:hexanes (1:1) and changing to (100%) afforded 1.73 g (85%) of compound (12) as a dark brown thick gum. IR (KBr) vmax. cm$^{-1}$: 3438, 3318 ($NH_2$), 3052 (Ar—H), 2911 (Alph-H), 1604, 1512, 1416 (C=C). $^1$H NMR (500 MHz, $CDCl_3$) δ=4.19 (s, 2H, $NH_2$); 4.42 (s, 2H, $CH_2$); 6.52 (d, 1H, J=8.2 Hz, H-3); 7.16 (dd, 1H, J=2.2, 8.2 Hz, H-4); 7.18 (d, 1H, J=2.2 Hz, H-6); $^{13}$C NMR (125.7 MHz, $CDCl_3$) δ=63.78 ($CH_2$), 109.56 (C-2), 117.51 (C-6), 126.57 (C-5), 131.58 (C-3/C-4), 131.86 (C-3/C-4), 145.06 (C-1). Calculated (%) for $C_7H_9BrN_2$ (199.99); C: 41.82, H: 4.51, N: 13.93. found (%); C: 41.74, H: 4.58, N: 13.84.

Example 4

Synthesis of 7-Bromo-3,4-dihydroquinazolin-2(1H)-one 13

To a solution of compound 12 (0.90 g, 4.5 mmol) in THF (10 mL) at room temperature was added CDI (0.80 g, 4.95 mmol), and the reaction was stirred at 80° C. for 6 hr. The mixture was cooled to room temperature, and the solid formed was filtered, washed with diethyl ether to afford 0.73 g (72%) of compound 13 as off-white solid. IR (KBr) vmax. cm$^{-1}$: 3308, 3158 (NH), 3022 (Ar—H), 1682 (C=O), 1514, 1411 (C=C). $^1$H NMR (500 MHz, DMSO-$d_6$) δ=5.25 (s, 2H, $CH_2$); 6.82 (d, 1H, J=8.2 Hz, H-5); 7.42 (m, 2H, H-4, H-6); 10.29 (br. s, 1H, NH); $^{13}$C NMR (125.7 MHz, DMSO-$d_6$)= 66.85 ($CH_2$), 113.70 (C-10), 115.70 (C-8), 121.03 (C-7), 127.52 (C-6), 131.41 (C-5), 135.88 (C-9), 151.42 (C=O). Calculated (%) for $C_8H_7BrN_2O$ (225.97); C: 42.32, H: 3.11, N: 12.34. found (%); C: 42.27, H: 3.16, N: 12.28.

Example 5

Synthesis of di-tert-Butyl 7-bromo-2-oxoquinazoline-1,3(2H,4H)-dicarboxylate 14

To a solution of compound (13) (0.6 g, 2.65 mmol) in anhydrous THF (15 mL) was added di-tert-butyl dicarbonate (2.31 g, 10.6 mmol), followed by the addition of 4-dimethylaminopyridine (0.32 g, 2.65 mmol), and the mixture was stirred overnight at room temperature. The mixture was diluted with ethyl acetate (25 mL) and washed successively with water (15 mL), brine (15 mL), dried over $Na_2SO_4$, and evaporated. Column chromatography on silica gel, eluting with ethyl acetate:hexanes (10:90) and then changing to (20:80), rendered 1.02 g (90%) of the title compound 14 as a colorless amorphous solid. IR (KBr) vmax. cm$^{-1}$: 3020 (Ar—H), 1688 (C=O), 1519, 1416 (C=C). $^1$H NMR (500 MHz, $CDCl_3$) δ=1.50 (s, 18H, 2($CH_3$)$_3$C); 5.12 (s, 2H, $CH_2$); 7.35 (d, 1H, J=2.1 Hz, H-8); 7.48 (dd, 1H, J=2.2, 8.2 Hz, H-6); 7.60 (d, 1H, J=8.2 Hz, H-5); $^{13}$C NMR (125.7 MHz, $CDCl_3$) δ=27.83 (($CH_3$)$_3$C), 60.40 ($CH_2$), 85.39 (($CH_3$)$_3$C), 118.32 (C-10), 122.05 (C-8), 126.26 (C-7), 127.50 (C-6), 131.68 (C-5), 134.52 (C-1), 149.95 (C=O), 155.33 (C=O). Calculated (%) for $C_{18}H_{23}BrN_2O_5$ (426.08); C: 50.60, H: 5.43, N: 6.56. found (%); C: 50.55, H: 5.48, N: 6.50.

Example 6

Synthesis of N-(2-Acetamido-4-bromobenzyl)acetamide 15

To a solution of compound (14) (0.5 g, 2.5 mmol) in pyridine (5 mL) was added acetic anhydride (0.95 mL, 10 mmol), and the reaction was stirred overnight at room temperature. To the mixture was added diethyl ether (20 mL), and the mixture was washed successively with $H_2O$ (10 mL), 1M HCl (10 mL), and brine (10 mL). The organic layer was dried over $Na_2SO_4$ and evaporated to obtain 0.70 g (99%) of compound 15 as an off-white solid. IR (KBr) vmax. cm$^{-1}$: 3312 (NH), 3042 (Ar—H), 1690 (C=O), 1522, 1410 (C=C). $^1$H NMR (500 MHz, $CDCl_3$) S=2.11 (s, 3H, $CH_3$); 2.23 (s, 3H, $CH_3$); 5.05 (s, 2H, $CH_2$); 7.46 (m, 2H, H-3, H-5); 7.89 (d, 1H, J=8.2 Hz, H-6). Calculated (%) for $C_{11}H_{13}BrN_2O_2$ (284.02); C: 46.33, H: 4.60, N: 9.82. found (%); C: 46.28, H: 4.63, N: 9.76.

Example 7

Synthesis of 4-Bromo-2-nitrobenzonitrile 17

To a cold solution of trifluoroacetic acid (18 mL) at 0° C. was added compound 8 (4.5 g, 23 mmol). After being stirred for 10 minutes, a solution of 33% hydrogen peroxide (7 mL, 67.8 mmol) was added, and the mixture was stirred at room temperature for 0.5 h, followed by stirring at 50° C. for 2 h. The mixture was poured into ice water, and the solid obtained was filtered and washed with cold water to afford 3.64 g (70%) of compound 17 as an off-white solid, m.p. 84-85° C.; IR (KBr) vmax, cm$^{-1}$: 3042 (Ar—H), 2252 (CN), 1520, 1412 (C=C). $^1$H NMR (500 MHz, DMSO-$d_6$) δ=8.15 (dd, 1H, J=2.4, 8.5 Hz, H-5); 8.25 (d, 1H, J=8.4 Hz, H-6); 8.46 (d, 1H, J=2.4 Hz, H-3); $^{13}$C NMR (125.7 MHz, DMSO-$d_6$) δ=108.88 (C-1), 114.54 (CN), 127.43 (C-3), 128.75 (C-4), 137.57 (C-5/C-6), 138.10 (C-5/C-6), 147.59 (C-2). Calculated (%) for $C_7H_3BrN_2O_2$ (225.94); C: 37.03, H: 1.33, N: 12.34. found (%); C: 37.00, H: 1.37, N: 12.27.

Example 8

Synthesis of tert-Butyl 4-(4-cyano-3-nitrophenyl)piperazine-1-carboxylate 18

To a solution of a mixture of compound 17 (3 g, 13.27 mmol) and 1-boc-piperazine hydrochloride (3.53 g, 15.92 mmol) in DMF (30 mL) was added $Et_3N$ (4.4 mL, 31.8 mmol), and the mixture was heated at 70° C. for 6 h. The mixture was cooled to room temperature, extracted with ethyl acetate (100 mL), and the organic layer was washed with brine (20 mL), dried over $Na_2SO_4$ and evaporated. Trituration with diethyl ether afforded 4.27 g (97%) of compound 18 as bright yellow solid, m.p. 138-139° C.; IR (KBr) vmax. cm$^{-1}$: 3042 (Ar—H), 2252 (CN), 1690 (C=O), 1610, 1520, 1412 (C=C). $^1$H NMR (500 MHz, DMSO-$d_6$) δ=1.39 (s, 9H, ($CH_3$)$_3$C); 3.44 (br. s, 4H, 2 $CH_2$); 7.19 (dd, 1H, J=2.6, 9.4 Hz, H-5); 7.46 (d, 1H, J=2.7 Hz, H-2); 8.17 (d, 1H, J=2.7 Hz, H-6); $^{13}$C NMR (125.7 MHz, DMSO-$d_6$) δ=28.11 (($CH_3$)$_3$C), 45.92 ($CH_2$), 46.02 ($CH_2$), 79.56 (($CH_3$)$_3$C), 109.24 (C-4), 115.61 (C-2), 116.46 (CN), 119.03 (C-6), 128.09 (C-5), 135.85 (C-3), 153.30 (C-1), 154.13 (C=O). Calculated (%) for $C_{16}H_{20}N_4O_4$ (332.15); C: 57.82, H: 6.07, N: 16.86. found (%); C: 57.76, H: 6.11, N: 16.80.

Example 9

Synthesis of tert-Butyl 4-(3-acetamido-4-(acetamidomethyl)phenyl)piperazine-1-carboxylate 19

To a solution of compound 18 (2.0 g, 6 mmol) in THF (30 mL) was added acetic anhydride (4.5 mL, 48 mmol), followed by the addition of Ra—Ni (~0.4 g), and the mixture was subjected to hydrogenation in a Parr apparatus at 60 psi for 12 h. After filtering over the pad of celite, the solution was concentrated to get a brown oil material, which was resolved over silica column eluting with EtOAc:hexanes (4:6) and then changing to (6:4) to get 1.75 g (75%) of 19 as an off-white gum. IR (KBr) vmax. cm': 3311, 3160 (NH), 3062 (Ar—H), 1691 (C=O), 1611, 1512, 1412 (C=C). $^1$H NMR (500 MHz, $CDCl_3$) δ=1.39 (s, 9H, $(CH_3)_3C$); 1.98 (s, 3H, $CH_3$); 2.21 (s, 3H, $CH_3$); 3.03 (m, 4H, $2CH_2$); 3.53 (m, 4H, $2CH_2$); 4.29 (d, 2H, J=6.7 Hz, $CH_2$); 6.73 (d, 1H, J=2.4 Hz, H-2); 6.84 (dd, 1H, J=8.8, J=2.4 Hz, H-6); 7.85 (d, 1H, J=8.8 Hz, H-5); 9.48 (s, 1H, NH); $^{13}$C NMR (125.7 MHz, $CDCl_3$) δ=22.96 ($CH_3$), 24.06 ($CH_3$), 28.37 $(CH_3)_3C$), 40.87 ($CH_2$), 43.50 ($CH_2$), 49.73 ($CH_2$), 79.95 $(CH_3)_3C$), 117.14 (C-2), 118.65 (C-4), 124.56 (C-6), 129.59 (C-3), 129.94 (C-5), 147.95 (C-1), 154.67 (C=O), 169.41 (C=O), 171.29 (C=O). Calculated (%) for $C_{20}H_{30}N_4O_4$ (390.23); C: 61.52, H: 7.74, N: 14.35. found (%); C: 61.43, H: 7.82, N: 14.26.

Example 10

Synthesis of tert-Butyl 4-(3-amino-4-(aminomethyl)phenyl)piperazine-1-carboxylate 20

To a solution of compound 19 (1.5 g, 3.85 mmol) in ethanol (20 mL) at room temperature was added a solution of KOH (3M, 25 mL), and the reaction was refluxed for 12 h. The reaction was cooled to room temperature, ice cold water was added, and the solution was extracted with ethyl acetate (30 mL×2). The organic layer was washed with brine (15 mL), dried over $Na_2SO_4$ and evaporated to get a brown oil material, which was resolved over silica column, eluting with ethyl acetate:hexanes (8:2), and then changing to ethyl acetate (100%) to obtain 0.98 g (83%) of 20 as a dark brown gum. IR (KBr) vmax. cm$^{-1}$: 3060 (Ar—H), 1690 (C=O), 1616, 1514, 1417 (C=C). $^1$H NMR (500 MHz, $CDCl_3$) δ=1.46 (s, 9H, $(CH_3)_3C$); 2.90 (m, 4H, $2CH_2$); 3.49 (m, 4H, $2CH_2$), 3.90 (s, 211, $CH_2$); 5.30 (br. s, 4H, $2NH_2$); 6.59 (d, 1H, J=8.2 Hz, H-5); 6.68 (dd, 1H, J=2.6, 8.2 Hz, H-6); 6.80 (d, 1H, J=2.6, H-2); $^{13}$C NMR (125.7 MHz, $CDCl_3$) δ=28.37 $(CH_3)_3C$), 42.10 ($CH_2$), 44.01 ($CH_2$), 50.87 ($CH_2$), 79.64 $(CH_3)_3C$), 117.29 (C-2), 117.79 (C-6), 119.88 (C-4), 120.36 (C-5), 139.80 (C-3), 144.15 (C-1), 154.67 (C=O). Calculated (%) for $C_{16}H_{26}N_4O_2$ (306.21); C: 62.72, 8.55, N: 18.29. found (%) C: 62.63, H: 8.63, N: 18.20.

Example 11

Synthesis of tert-Butyl 4-(2-oxo-1,2,3,4-tetrahydroquinazolin-7-yl)piperazine-1-carboxylate 16

Following the same procedure adopted for the synthesis of compound 13, reaction of compound 20 with CDI afforded 0.73 g (75%) of compound 16 as an off-white solid, m.p. 218-219° C.; IR (KBr) vmax. cm$^{-1}$: 3211, 3166 (NH), 3037 (Ar—H), 1693 (C=O), 1610, 1519, 1417 (C=C). $^1$H NMR (500 MHz, $CDCl_3$) S=1.48 (s, 9H, $(CH_3)_3C$); 3.00 (m, 4H, $2CH_2$); 3.56 (m, 4H, $2CH_2$); 4.48 (s, 2H, $CH_2$); 6.62 (d, 1H, J=2.5 Hz, H-8); 6.64 (d, 1H, J=8.5 Hz, H-5); 6.74 (dd, 1H, J=2.5, 8.4 Hz, H-6); 7.80 (br.s, 1H, NH); $^{13}$C NMR (125.7 MHz, $CDCl_3$) δ=28.65 $(CH_3)_3C$), 43.31 ($CH_2$), 43.98 ($CH_2$), 50.63 ($CH_2$), 80.18 $(CH_3)_3C$), 115.13 (C-8/C-6), 115.21 (C-8/C-6), 117.59 (C-5), 118.35 (C-5), 130.66 (C-5), 147.20 (C-5), 154.91 (C=O), 155.95 (C=O). Calculated (%) for $C_{17}H_{24}N_4O_3$ (332.18); C: 61.43, H: 7.28, N: 16.86. found (%) C: 61.37, H: 7.32, N: 16.80.

Example 12

Synthesis of 7-(Piperazin-1-yl)-3,4-dihydroquinazolin-2(1H)-one 5

To a solution of 16 (0.7 g, 2.11 mmol) in a mixture of $CH_2Cl_2$ (15 mL) and THF (5 mL) at 0° C. was added TFA (5 mL) and the mixture was stirred at room temperature for 6 h. The solvent was evaporated under vacuum to afford 0.66 g (96%) of compound 5 as a dark brown gum. IR (KBr) vmax. cm$^{-1}$: 3261 (NH), 3032 (Ar—H), 1691 (C=O), 1613, 1513, 1415 (C=C). $^1$H NMR (500 MHz, DMSO-$d_6$) δ=3.18 (m, 4H, $2CH_2$); 3.42 (m, 4H, $2CH_2$); 4.23 (s, 2H, $CH_2$); 6.66 (m, 2H, aromatic-H); 6.73 (m, 1H, aromatic-H); 8.80 (br. s, 1H, NH); 8.86 (br. s, 1H, NH); $^{13}$C NMR (125.7 MHz, DMSO-$d_6$) δ=46.35 ($CH_2$), 46.73 ($CH_2$), 48.63 ($CH_2$), 114.19 (aromatic-C), 114.38 (aromatic-C), 116.49 (aromatic-C), 118.83 (aromatic-C), 131.87 (aromatic-C), 144.81 (aromatic-C), 154.72 (C=O). Calculated (%) for $C_{14}H_{16}F_3N_4O_2$ (329.12); C: 48.56, H: 4.95, N: 16.18. found (%); C: 48.45, H: 5.05, N: 16.15.

Example 13

Synthesis of tert-Butyl 4-(2-oxo-1,2,3,4-tetrahydroquinazolin-7-yl)-5,6-dihydropyridine-1(2H)-carboxylate 22

To a nitrogen flushed flask containing the boronate 21 (1.39 g, 4.5 mmol), $K_2CO_3$ (1.86 g, 13.5 mmol) and $PdCl_2$ dppf (0.23 g, 0.28 mmol) was added a solution of the bromide 13 (1.07 g, 4.74 mmol) in DMF (30 mL). The mixture was deoxygenated by continued flushing with nitrogen. The mixture was then heated to 80° C. and stirred under $N_2$ overnight when TLC indicated completion of the reaction. After cooling, ethyl acetate (40 mL) and water (20 mL) were added, and the organic phase was separated. The water phase was extracted with ethyl acetate (20 mL). The combined organic phases were washed with brine, dried over $Na_2SO_4$, filtered over a short plug of celite, and evaporated under reduced pressure. Column chromatography on silica gel, eluting with hexanes:ethyl acetate (6:4), and then changing to (4:6)) afforded 0.85 g (55%) of compound 22 as an off-white solid, m.p. 183-184° C.; IR (KBr) vmax. cm$^{-1}$: 3261, 3155 (NH), 3052 (Ar—H), 1695 (C=O), 1616, 1518, 1415 (C=C). $^1$H-NMR (500 MHz, $CDCl_3$) δ=1.49 (s, 9H, $(CH_3)_3C$); 1.72 (br, s, 2H, $CH_2$); 2.47 (br. s, 2H, $CH_2$); 3.63 (m, 211, $CH_2$); 4.07 (s, 2H, $CH_2$); 5.97 (br. s, 1H, CH); 6.76 (d, J=8.2 Hz, 1H, 11-5); 7.12 (br. s, 1H, H-8); 7.28 (m, 1H, H-6); 7.65 (br. s, 1H, NH); $^{13}$C NMR (125.7 MHz, $CDCl_3$) δ=27.39 ($CH_2$), 28.48 $(CH_3)_3C$), 29.71 ($CH_2$), 41.90 ($CH_2$), 68.73 ($CH_2$), 79.80 $(CH_3)_3C$), 113.87 (aromatic-C), 118.03 (aromatic-C), 120.92 (aromatic-C), 125.75 (aromatic-C), 134.49 (aromatic-C), 136.34 (aromatic-C), 152.59 (C=O), 154.88 (C=O). Calcu-

Example 14

Synthesis of tert-Butyl 4-(2-oxo-1,2,3,4-tetrahydroquinazolin-7-yl)piperidine-1-carboxylate 23

To a solution of compound 22 (0.8 g, 2.45 mmol) in THF (20 mL) was added Pd—C (10% wet basis, 0.15 g), and the mixture was subjected to hydrogenation in a Parr apparatus at 60 psi for 12 h. After filtering over the pad of celite, the solution was concentrated to get a brown oil material, which was resolved over silica column, eluting with hexanes:ethyl acetate (4:6) and then changing to (6:4) yielded 0.59 g (76%) of 23 as a light yellow gum. IR (KBr) vmax. cm$^{-1}$: 3211, 3165 (NH), 3072 (Ar—H), 1698 (C=O), 1610, 1512, 1419 (C=C). $^1$H-NMR (500 MHz, CDCl$_3$) δ=1.48 (s, 9H, (CH$_3$)$_3$C); 1.54 (m, 2H, CH$_2$); 1.75-1.82 (m, 2H, CH$_2$); 2.56 (m, 1H, CH); 2.76 (br. s, 2H, CH$_2$); 4.23 (br. s, 2H, CH$_2$); 4.44 (s, 2H, CH$_2$); 6.58 (m, 2H, H-7, H-8); 7.30 (m, 1H, d, J=8.3 Hz, H-5); $^{13}$C NMR (125.7 MHz, CDCl$_3$) δ=28.38 (CH$_3$)$_3$C), 32.50 (CH$_2$), 42.87 (CH$_2$), 43.30 (CH), 47.88 (CH$_2$), 66.36 (CH$_2$), 79.53 (CH$_3$)$_3$C), 93.98 (aromatic-C), 113.24 (aromatic-C), 116.97 (aromatic-C), 117.68 (aromatic-C), 132.41 (aromatic-C), 134.49 (aromatic-C), 149.82 (aromatic-C), 152.48 (C=O), 154.69 (C=O). Calculated (%) for C$_{18}$H$_{25}$N$_3$O$_3$ (331.19); C: 65.23, 7.60, N: 12.68. found (%); C: 65.12, H: 7.69, N: 12.55.

Example 15

Synthesis of tert-Butyl 4-(3-amino-4-cyanophenyl)-5,6-dihydropyridine-1(2H)-carboxylate 24

Following the same procedure adopted for the synthesis of 22, the reaction of nitrile 11 with boronic ester 21 afforded the title compound 24 as an off-white solid (62%). IR (KBr) vmax, cm$^{-1}$: 3421, 3318 (NH$_2$), 3072 (Ar—H), 2247 (CN), 1691 (C=O), 1616, 1510, 1412 (C=C). $^1$H-NMR (500 MHz, CDCl$_3$) δ=1.49 (s, 9H, (CH$_3$)$_3$C); 1.71 (br, s, 2H, CH$_2$); 2.45 (br. s, 2H, CH$_2$); 3.61 (m, 2H, CH$_2$); 4.07 (s, 2H CH$_2$); 4.43 (br. s, 2H, NH$_2$); 6.10 (br. s, 1H, CH); 6.71 (d, J=2.2 Hz, 1H, H-2); 6.75 (dd, 1H, J=2.3, 8.6 Hz, H-6); 7.33 (d, J=8.5 Hz, 1H, H-5); 8.01 (br. s, 1H, NH); $^{13}$C NMR (125.7 MHz, CDCl$_3$) δ=27.35 (CH$_2$), 28.47 (CH$_3$)$_3$C), 29.73 (CH$_2$), 41.96 (CH$_2$), 79.91 (CH$_3$)$_3$C), 94.63 (aromatic-C), 115.12 (aromatic-C), 117.69 (CN), 133.67 (aromatic-C), 147.42 (aromatic-C), 150.47 (aromatic-C), 155.33 (C=O). Calculated (%) for C$_{17}$H$_{21}$N$_3$O$_2$ (299.16); C: 68.20, H: 7.07, N: 14.04. found (%); C: 68.16, H: 7.13, N: 13.97.

Example 16

Synthesis of tert-Butyl 4-(3-acetamido-4-(acetamidomethyl)phenyl)piperidine-1-carboxylate 25

Following the same procedure adopted for the synthesis of 19, hydrogenation of compound 24 afforded compound 25 as a light brown gum (87%). IR (KBr) vmax. cm$^{-1}$: 3218 (NH), 3062 (Ar—H), 1690 (C=O), 1611, 1515, 1419 (C=C). $^1$H NMR (500 MHz, CDCl$_3$) δ=1.47 (s, 9H, (CH$_3$)$_3$C); 1.57 (m, 2H, CH$_2$); 1.75-1.83 (m, 2H, CH$_2$); 1.98 (s, 3H, CH$_3$); 2.21 (s, 3H, CH$_3$); 2.55 (m, 1H, CH); 2.74 (br. s, 2H, CH$_2$); 4.20 (br. s, 2H, CH$_2$); 4.41 (s, 2H, CH$_2$); 6.79-6.84 (m, 2H, H-2, H-6); 7.83 (d, 1H, J=8.8 Hz, H-5); 9.40 (s, 1H, NH); $^{13}$C NMR (125.7 MHz, CDCl$_3$) δ=22.95 (CH$_3$), 32.52 (CH$_2$), 42.85 (CH$_2$), 43.38 (CH), 47.80 (CH$_2$), 49.88 (CH$_2$), 79.58 (CH$_3$)$_3$C), 117.19 (aromatic-C), 118.67 (aromatic-C), 124.59 (aromatic-C), 129.79 (aromatic-C), 129.96 (aromatic-C), 147.93 (aromatic-C), 154.62 (C=O), 169.42 (C=O), 171.27 (C=O). Calculated (%) for C$_{21}$H$_{31}$N$_3$O$_4$ (389.23); C: 64.76, H: 8.02, N: 10.79. found (%); C: 64.70, H: 8.08, N: 10.72.

Example 17

Synthesis of tert-Butyl 4-(3-amino-4-(aminomethyl)phenyl)piperidine-1-carboxylate 26

Following the same procedure adopted for the synthesis of 20, basic hydrolysis of compound 25 afforded compound 26 as a brown gum (89%). IR (KBr) vmax. cm$^{-1}$: 3431, 3319 (NH$_2$), 3048 (Ar—H), 1689 (C=O), 1611, 1516, 1412 (C=C). $^1$H NMR (500 MHz, CDCl$_3$) δ=1.47 (s, 9H, (CH$_3$)$_3$C); 1.64 (m, 2H, CH$_2$); 1.79-1.88 (m, 2H, CH$_2$); 2.65 (m, 1H, CH); 2.83 (br. s, 2H, CH$_2$); 3.86 (br. s, 2H, CH$_2$); 3.95 (s, 2H, CH$_2$); 5.36 (br. s, 4H, 2NH$_2$); 6.71-6.76 (m, 2H, H-2, H-6); 7.21 (d, 1H, J=8.8 Hz, H-5); $^{13}$C NMR (125.7 MHz, CDCl$_3$) δ=28.38 (CH$_3$)$_3$C), 32.47 (CH$_2$), 42.77 (CH$_2$), 43.32 (CH), 47.93 (CH$_2$), 50.46 (CH$_2$), 79.78 (CH$_3$)$_3$C), 117.02 (aromatic-C), 118.27 (aromatic-C), 124.50 (aromatic-C), 129.82 (aromatic-C), 129.26 (aromatic-C), 146.83 (aromatic-C), 154.60 (C=O). Calculated (%) for C$_{17}$H$_{27}$N$_3$O$_2$ (305.21); C: 66.85, H: 8.91, N: 13.76. found (%); C: 66.75, H: 8.99, N: 13.66.

Example 18

Synthesis of 7-(piperidin-4-yl)-3,4-dihydroquinazolin-2(1H)-one 6

Following the same procedure adopted for the synthesis of 5, treatment of compound 23 with trifluoroacetic acid afforded the title compound 6 as a dark brown gum (95%). IR (KBr) vmax. cm$^{-1}$: 3271 (NH), 3032 (Ar—H), 1688 (C=O), 1610, 1515, 1412 (C=C). $^1$H NMR (500 MHz, CDCl$_3$) δ=1.71 (m, 2H, CH$_2$); 1.85 (m, 2H, CH$_2$); 2.75 (m, 1H, CH); 2.95 (m, 2H, CH$_2$); 3.32 (m, 2H, CH$_2$); 5.23 (s, 2H, CH$_2$); 6.82 (d, 1H, J=8.2 Hz, aromatic H); 7.02 (s, 1H, aromatic H); 7.09 (d, 1H, J=8.1 Hz, aromatic H); 8.61 (br. s, 1H, NH); 8.87 (br. s, 1H, NH); 10.11 (s, 1H, NH); $^{13}$C NMR (125.7 MHz, CDCl$_3$) δ=29.51 (CH$_2$), 38.34 (CH), 43.54 (CH$_2$), 67.61 (CH$_2$), 113.81 (aromatic-C), 118.68 (aromatic-C), 122.45 (aromatic-C), 126.84 (aromatic-C), 134.96 (aromatic-C), 138.77 (aromatic-C), 151.86 (C=O). Calculated (%) for C$_{15}$H$_{17}$F$_3$N$_3$O$_2$ (328.13); C: 52.17, H: 5.25, N: 12.17. found (%); C: 52.08, H: 5.33, N: 12.07.

Example 19

Synthesis of 7-(4-(biphenyl-4-ylmethyl)piperazin-1-yl)-3,4-dihydroquinazolin-2(1H)-one 5a Representative procedure: To a solution of compound 5 (0.15 g, 0.43 mmol) and biphenyl-4-carbaldehyde (a) (0.1 g, 0.55 mmol) in DMSO (2 mL) at 0° C. was added Et$_3$N (0.13 mL, 0.97 mmol). After being stirred for 0.5 h at room temperature, NaBH(OAc)$_3$ (0.11 g, 0.53 mmol) was added, and the mixture was stirred for 6 h. Sat. NaHCO$_3$ solution (5 mL) was added and stirred for 15 min, followed by the addition of ethyl acetate (20 mL). The organic layer was separated and washed with sat. NaHCO$_3$, brine, and dried over Na$_2$SO$_4$ and evaporated. Column chromatography on silica gel, eluting with methanol:dichloromethane (5:95) and then changing to 10:90 afforded 0.099 g (58%) of compound 5a as an off-white solid, m.p. 134-135° C.; IR (KBr) vmax. cm$^{-1}$: 3431 (NH), 3062 (Ar—H), 2963 (Alph-H), 1703 (C═O), 1620, 1512, 1430 (C═C), 1221 (C—N), 1168 (C—O). $^1$H NMR (500 MHz, DMSO-d$_6$) δ=2.71 (m, 4H, 2CH$_2$); 3.14 (m, 4H, 2CH$_2$); 3.68 (s, 2H, CH$_2$); 4.47 (s, 2H, CH$_2$); 6.64 (d, 1H, J=2.3 Hz, aromatic H); 6.68 (d, 1H, J=8.3 Hz, aromatic H); 6.78 (dd, 1H, J=2.2, 8.4 Hz, aromatic H); 7.43-7.48 (m, 5H, aromatic H); 7.58-7.61 (m, 4H, aromatic H); $^{13}$C NMR (125.7 MHz, DMSO-d$_6$) δ=43.78 (CH$_2$), 50.11 (CH$_2$), 53.02 (CH$_2$), 62.69 (CH$_2$), 98.21 (aromatic-C), 114.64 (aromatic-C), 115.15 (aromatic-C), 117.28 (aromatic-C), 118.25 (aromatic-C), 127.18 (aromatic-C), 127.28 (aromatic-C), 127.53 (aromatic-C), 127.91 (aromatic-C), 128.97 (aromatic-C), 129.21 (aromatic-C), 130.29 (aromatic-C), 130.57 (aromatic-C), 140.92 (aromatic-C), 147.12 (aromatic-C), 156.34 (C═O). Calculated (%) for C$_{25}$H$_{26}$N$_4$O (398.21); C: 75.35, H: 6.58, N: 14.06. found (%); C: 75.28, H: 6.64, N: 13.97.

Example 20

Synthesis of 7-(4-((4'-fluorobiphenyl-4-yl)methyl) piperazin-1-yl)-3,4-dihydroquinazolin-2(1H)-one 5b Following the same procedure adopted for the synthesis of 5a, the reductive amination of compound 5 with the aldehyde of b afforded 0.11 g (60%) of compound 5b as an off-white solid, m.p. 220-221° C.; IR (KBr) vmax. cm$^{-1}$: 3428 (NH), 3042 (Ar—H), 2953 (Alph-H), 1701 (C═O), 1621, 1512, 1420 (C═C), 1220 (C—N), 1158 (C—O). $^1$H NMR (500 MHz, DMSO-d$_6$) δ=2.72 (m, 4H, 2CH$_2$); 3.14 (m, 4H, 2CH$_2$); 3.67 (s, 2H, CH$_2$); 4.47 (s, 2H, CH$_2$); 6.64 (d, 1H, J=2.3 Hz, aromatic H); 6.69 (d, 1H, J=8.3 Hz, aromatic H); 6.80 (dd, 1H, J=2.2, 8.4 Hz, aromatic H); 7.13-7.15 (m, 2H, aromatic H); 7.42-7.45 (m, 2H, aromatic H); 7.48-7.57 (m, 4H, aromatic H); $^{13}$C NMR (125.7 MHz, DMSO-d$_6$) δ=44.16 (CH$_2$), 50.60 (CH$_2$), 53.46 (CH$_2$), 63.12 (CH$_2$), 115.11 (aromatic-C), 115.59 (aromatic-C), 116.10 (aromatic-C), 116.29 (aromatic-C), 117.74 (aromatic-C), 118.78 (aromatic-C), 127.59 (aromatic-C), 129.19 (aromatic-C), 129.26 (aromatic-C), 130.81 (aromatic-C), 131.05 (aromatic-C), 135.21 (aromatic-C), 147.55 (aromatic-C), 156.32 (C═O), 161.68 (aromatic-C). Calculated (%) for C$_{25}$H$_{25}$FN$_4$O (416.20); C: 72.09, H: 6.05, N: 13.45. found (%); C: 72.01, H: 6.11, N: 13.37.

Example 21

Synthesis of 7-(4-((5-phenylpyridin-3-yl)methyl) piperazin-1-yl)-3,4-dihydroquinazolin-2(1H)-one 5c Following the same procedure adopted for the synthesis of 5a, the reductive amination of compound 5 with the aldehyde of c afforded 0.082 g (48%) of compound 5c as light yellow gum. IR (KBr) vmax. cm$^{-1}$: 3438, 3190 (NH), 3048 (Ar—H), 2939 (Alph-H), 1688 (C═O), 1629, 1508, 1443 (C═C), 1173 (C—O). $^1$H NMR (500 MHz, CDCl$_3$) δ=2.65 (br. s, 4H, 2CH$_2$); 3.10 (m, 4H, 2CH$_2$); 3.65 (s, 2H, CH$_2$); 4.47 (s, 2H, CH$_2$); 6.60-6.64 (m, 2H, aromatic H); 6.73 (dd, 1H, J=2.2, 8.4 Hz, aromatic H); 7.13-7.15 (m, 2H, aromatic H); 7.42-7.45 (m, 2H, aromatic H); 7.42-7.46 (m, 3H, aromatic H); 7.60 (m, 2H, aromatic H); 7.90 (s, 1H, aromatic H); 8.54 (s, 1H, aromatic H); 8.91 (s, 1H, aromatic H); $^{13}$C NMR (125.7 MHz, CDCl$_3$) δ=43.67 (CH$_2$), 49.81 (CH$_2$), 52.78 (CH$_2$), 59.80 (CH$_2$), 113.95 (aromatic-C), 114.61 (aromatic-C), 116.48 (aromatic-C), 117.80 (aromatic-C), 126.81 (aromatic-C), 126.91 (aromatic-C), 127.87 (aromatic-C), 128.37 (aromatic-C), 128.71 (aromatic-C), 128.79 (aromatic-C), 128.79 (aromatic-C), 132.99 (aromatic-C), 133.14 (aromatic-C), 134.84 (aromatic-C), 136.12 (aromatic-C), 136.47 (aromatic-C), 137.38 (aromatic-C), 146.08 (aromatic-C), 146.74 (aromatic-C), 148.84 (aromatic-C), 155.40 (C═O). Calculated (%) for C$_{24}$H$_{25}$N$_5$O (399.21); C: 72.16, H: 6.31, N: 17.53. found (%); C: 72.07, H: 6.39, N: 17.41.

Example 22

Synthesis of 7-(4-((5-(4-fluorophenyl)pyridin-3-yl) methyl)piperazin-1-yl)-3,4-dihydroquinazolin-2 (1H)-one (5d)

Following the same procedure adopted for the synthesis of 5a, the reductive amination of compound 5 with the aldehyde of d afforded 0.080 g (47%) of compound 5d as a light yellow solid, m.p. 180-181° C.; IR (KBr) vmax. cm$^{-1}$: 3428, 3180 (NH), 3047 (Ar—H), 2969 (Alph-H), 1689 (C═O), 1622, 1512, 1423 (C═C), 1170 (C—O). $^1$H NMR (500 MHz, CDCl$_3$) δ=2.69 (br. s, 4H, 2CH$_2$); 3.11 (m, 4H, 2CH$_2$); 3.66 (s, 2H, CH$_2$); 4.47 (s, 2H, CH$_2$); 6.60-6.66 (m, 2H, aromatic H); 6.72 (dd, 1H, J=2.2, 8.4 Hz, aromatic H); 7.16-7.19 (m, 2H, aromatic H); 7.55-7.59 (m, 2H, aromatic H); 7.87 (s, 1H, aromatic H); 8.52 (s, 1H, aromatic H); 8.71 (s, 1H, NH); 8.95 (s, 1H, aromatic H); $^{13}$C NMR (125.7 MHz, CDCl$_3$) δ=43.64 (CH$_2$), 49.71 (CH$_2$), 52.75 (CH$_2$), 59.68 (CH$_2$), 114.12 (aromatic-C), 114.57 (aromatic-C), 115.74 (aromatic-C), 115.91 (aromatic-C), 116.73 (aromatic-C), 117.84 (aromatic-C), 128.58 (aromatic-C), 129.70 (aromatic-C), 134.85 (aromatic-C), 135.28 (aromatic-C), 146.66 (aromatic-C), 146.94 (aromatic-C), 148.81 (aromatic-C), 150.47 (aromatic-C), 152.78 ((aromatic-C)), 155.08 (C═O), 161.71 (aromatic-C), 163.69 (aromatic-C). Calculated (%) for C$_{24}$H$_{24}$FN$_5$O (417.20); C: 69.05, H: 5.79, N: 16.78. found (%); C: 68.97, H: 5.85, N: 16.70.

Example 23

Synthesis of 7-(4-(3-cyclopentenylbenzyl)piperazin-1-yl)-3,4-dihydroquinazolin-2(1H)-one 5e Following the same procedure adopted for the synthesis of 5a, the reductive amination of compound 5 with the aldehyde of e afforded 0.120 g (65%) of compound 5e as a light brown gum. IR (KBr) vmax. cm$^{-1}$: 3418, 3186 (NH), 3047 (Ar—H), 2939 (Alph-H), 1691 (C═O), 1620, 1513, 1423 (C═C), 1168 (C—O). $^1$H NMR (500 MHz, CDCl$_3$) δ=2.00-2.03 (m, 2H, CH$_2$); 2.52 (m, 2H, CH$_2$); 2.61 (m, 4H, 2CH$_2$); 2.71 (m, 2H, CH$_2$); 3.09 (m, 4H, 2CH$_2$); 3.56 (s, 2H, CH$_2$); 4.47 (s, 2H, CH$_2$); 5.62 (br. s, 1H, NH); 6.20 (s, 1H, CH); 6.59 (d, 1H, J=2.3 Hz, aromatic H); 6.62 (d, 1H, J=8.3 Hz, aromatic H); 6.73 (dd, 1H, J=2.2, 8.4 Hz, aromatic H); 7.19 (m, 1H, aromatic H); 7.26 (m, 1H, aromatic H), 7.33 (m, 1H, aromatic H); 7.41 (s, 1H, aromatic H); 7.94 (br. s, 1H, NH); $^{13}$C NMR (125.7 MHz, CDCl$_3$) δ=23.50 (CH$_2$), 33.45 (CH$_2$), 33.55 (CH$_2$), 44.13 (CH$_2$), 50.27 (CH$_2$), 53.22 (CH$_2$), 62.65 (CH$_2$), 114.36 (aromatic-C), 115.15 (aromatic-C), 116.91 (aromatic-C), 118.23 (aromatic-C), 124.72 (aromatic-C), 126.57 (aromatic-C), 128.02 (aromatic-C), 128.49 (aromatic-C), 130.07 (aromatic-C), 137.76 (aromatic-C), 142.54 (aromatic-C), 147.32 (aromatic-C), 156.15 (C═O). Calculated (%) for C$_{24}$H$_{28}$N$_4$O (388.23); C: 74.20, H: 7.26, N: 14.42. found (%); C: 74.10, H: 7.34, N: 14.33.

Example 24

Synthesis of 7-(4((5-cyclopentenylpyridin-3-yl)methyl)piperazin-1-yl)-3,4-dihydroquinazolin-2(1H)-one 5f

Following the same procedure adopted for the synthesis of 5a, the reductive amination of compound 5 with the aldehyde of f afforded 0.092 g (55%) of compound 5f as an off-white solid, m.p. 185-186° C.; IR (KBr) vmax. cm$^{-1}$: 3408, 3196 (NH), 3067 (Ar—H), 2969 (Alph-H), 1690 (C=O), 1630, 1523, 1420 (C=C), 1172 (C—O). $^1$H NMR (500 MHz, CDCl$_3$) δ=2.00-2.03 (m, 2H, CH$_2$); 2.55 (m, 2H, CH$_2$); 2.62 (m, 4H, 2CH$_2$); 2.71 (m, 2H, CH$_2$); 3.08 (m, 4H, 2CH$_2$); 3.56 (s, 2H, CH$_2$); 4.46 (s, 2H, CH$_2$); 5.62 (br. s, 1H, NH); 6.20 (s, 1H, CH); 6.58 (d, 1H, J=2.3 Hz, aromatic H); 6.63 (d, 1H, J=8.3 Hz, aromatic H); 6.72 (dd, 1H, J=2.2, 8.4 Hz, aromatic H); 6.72 (m, 1H, aromatic H); 7.70 (s, 1H, NH); 8.06 (s, 1H, aromatic H), 8.40 (s, 1H, aromatic H), 8.59 (s, 1H, aromatic H); $^{13}$C NMR (125.7 MHz, CDCl$_3$) δ=24.15 (CH$_2$), 33.87 (CH$_2$), 34.30 (CH$_2$), 44.83 (CH$_2$), 50.99 (CH$_2$), 53.22 (CH$_2$), 62.65 (CH$_2$), 115.12 (aromatic-C), 115.90 (aromatic-C), 117.66 (aromatic-C), 118.98 (aromatic-C), 124.45 (aromatic-C), 130.90 (aromatic-C), 133.05 (aromatic-C), 133.66 (aromatic-C), 134.32 (aromatic-C), 140.31 (aromatic-C), 147.03 (aromatic-C), 147.90 (aromatic-C), 149.45 (aromatic-C), 156.91 (C=O). Calculated (%) for C$_{23}$H$_{27}$N$_5$O (389.22); C: 70.92, H: 6.99, N: 17.98. found (%); C: 70.85, H: 7.05, N: 17.90.

Example 24

Synthesis of 7-(1-(biphenyl-4-ylmethyl)piperidin-4-yl)-3,4-dihydroquinazolin-2(1H)-one 6a

Following the same procedure adopted for the synthesis of 5a, the reductive amination of compound 6 with the aldehyde of a afforded 0.110 g (59%) of compound 6a as a light brown solid, m.p. 125-126° C.; IR (KBr) vmax. cm$^{-1}$: 3428 (NH), 3057 (Ar—H), 2959 (Alph-H), 1691 (C=O), 1622, 1513, 1415 (C=C), 1170 (C—O). $^1$H NMR (500 MHz, CDCl$_3$) δ=1.79-1.84 (m, 4H, 2CH$_2$); 2.04-2.14 (m, 2H, CH$_2$); 2.46 (m, 1H, CH); 3.07 (m, 2H, CH$_2$); 3.64 (s, 2H, CH$_2$); 5.27 (s, 2H, CH$_2$); 6.79 (d, J=8.2 Hz, 1H, aromatic H); 6.94 (br. s, 1H, aromatic H); 7.08 (d, 1H, J=8.2 Hz, aromatic H); 7.40-7.44 (m, 4H, aromatic H); 7.55-7.60 (m, 4H, aromatic H); 9.03 (br. s, 1H, NH); $^{13}$C NMR (125.7 MHz, CDCl$_3$) δ=33.14 (CH$_2$), 41.74 (CH$_2$), 45.20 (CH), 53.69 (CH$_2$), 62.63 (CH$_2$), 68.66 (CH$_2$), 114.05 (aromatic-C), 117.80 (aromatic-C), 122.29 (aromatic-C), 126.90 (aromatic-C), 126.93 (aromatic-C), 127.13 (aromatic-C), 127.46 (aromatic-C), 128.66 (aromatic-C), 129.79 (aromatic-C), 133.78 (aromatic-C), 136.44 (aromatic-C), 140.00 (aromatic-C), 140.75 (aromatic-C), 141.37 (aromatic-C), 153.51 (C=O). Calculated (%) for C$_{26}$H$_{27}$N$_3$O (397.22); C: 78.56, H: 6.85, N: 10.57. found (%); C: 78.50, H: 6.91, N: 10.48.

Example 26

Synthesis of 7-(1-((4'-fluorobiphenyl-4-yl)methyl)piperidin-4-yl)-3,4-dihydroquinazolin-2(1H)-one (6b)

Following the same procedure adopted for the synthesis of 5a, the reductive amination of compound 6 with the aldehyde of b afforded 0.086 g (52%) of compound 6b as an off-white solid, m.p. 160-161° C.; IR (KBr) vmax. cm$^{-1}$: 3403, 3186 (NH), 3077 (Ar—H), 2962 (Alph-H), 1693 (C=O), 1620, 1518, 1416 (C=C), 1173 (C—O). $^1$H NMR (500 MHz, CDCl$_3$) δ=1.80 (hr. s, 4H, 2CH$_2$); 2.19 (m, 2H, CH$_2$); 2.49 (m, 1H, CH); 3.09 (m, 2H, CH$_2$); 3.64 (s, 2H, CH$_2$); 5.26 (s, 2H, CH$_2$); 6.82 (d, 1H, J=8.3 Hz, aromatic H); 6.94 (br. s, 1H, aromatic H); 7.09-7.13 (m, 3H, aromatic H); 7.42 (m, 2H, aromatic H); 7.49-7.56 (m, 4H, aromatic H); 9.19 (br. s, 1H, NH); $^{13}$C NMR (125.7 MHz, CDCl$_3$) δ=33.09 (CH$_2$), 41.69 (CH$_2$), 45.55 (CH), 53.77 (CH$_2$), 62.54 (CH$_2$), 68.50 (CH$_2$), 114.10 (aromatic-C), 115.41 (aromatic-C), 117.83 (aromatic-C), 126.74 (aromatic-C), 127.40 (aromatic-C), 128.42 (aromatic-C), 129.82 (aromatic-C), 133.86 (aromatic-C), 136.85 (aromatic-C), 139.07 (aromatic-C), 141.18 (aromatic-C), 153.30 (C=O), 161.31 (aromatic-C), 163.27 (aromatic-C). Calculated (%) for C$_{26}$H$_{26}$FN$_3$O (415.21); C: 75.16, H: 6.31, N: 10.11. found (%); C: 75.10, H: 6.36, N: 10.02.

Example 27

Synthesis of 7-(1-((5-phenylpyridin-3-yl)methyl)piperidin-4-yl)-3,4-dihydroquinazolin-2(1H)-one 6c

Following the same procedure adopted for the synthesis of 5a, the reductive amination of compound 6 with the aldehyde of c afforded 0.082 g (50%) of compound 6c as a light brown gum. IR (KBr) vmax. cm$^{-1}$: 3413, 3180 (NH), 3057 (Ar—H), 2960 (Alph-H), 1691 (C=O), 1631, 1528, 1426 (C=C), 1172 (C—O). $^1$H NMR (500 MHz, CDCl$_3$) δ=1.80 (br. s, 4H, 2CH$_2$); 2.19 (m, 2H, CH$_2$); 2.49 (m, 1H, CH); 3.07 (m, 2H, CH$_2$); 3.68 (s, 2H, CH$_2$); 5.29 (s, 2H, CH$_2$); 6.80 (d, 1H, J=8.2 Hz, aromatic H); 6.94 (br. s, 1H, aromatic H); 7.08 (d, 1H, J=8.2 Hz, aromatic H); 7.39 (m, 1H, aromatic H); 7.46 (m, 2H, aromatic H); 7.59 (m, 2H, aromatic H); 7.94 (s, 1H, aromatic H); 8.54 (s, 1H, aromatic H); 8.77 (s, 1H, aromatic H); 9.20 (br. s, 1H, NH); $^{13}$C NMR (125.7 MHz, CDCl$_3$) δ=33.05 (CH$_2$), 41.55 (CH), 53.82 (CH$_2$), 60.03 (CH$_2$), 68.56 (CH$_2$), 114.09 (aromatic-C), 117.85 (aromatic-C), 122.31 (aromatic-C), 127.06 (aromatic-C), 127.38 (aromatic-C), 128.05 (aromatic-C), 128.94 (aromatic-C), 133.98 (aromatic-C), 135.34 (aromatic-C), 136.34 (aromatic-C), 137.43 (aromatic-C), 140.98 (aromatic-C), 146.94 (aromatic-C), 148.89 (aromatic-C), 153.30 (C=O). Calculated (%) for C$_{25}$H$_{26}$N$_4$O (398.21); C: 75.35, H; 6.58, N: 14.06. found (%); C: 71.28, H: 6.68, N: 13.93.

Example 28

Synthesis of 7-(1-((5-(4-fluorophenyl)pyridin-3-yl)methyl)piperidin-4-yl)-3,4-dihydroquinazolin-2(1H)-one 6d

Following the same procedure adopted for the synthesis of 5a, the reductive amination of compound 6 with the aldehyde of d afforded 0.082 g (50%) of compound 6d as a light yellow gum. IR (KBr) vmax. cm$^{-1}$: 3338, 3196 (NH), 3051 (Ar—H), 2935 (Alph-H), 1692 (C=O), 1621, 1517, 1418 (C=C), 1178 (C—O). $^1$H NMR (500 MHz, CDCl$_3$) δ=1.79 (br. s, 4H, 2CH$_2$); 2.09 (m, 2H, CH$_2$); 2.48 (m, 1H, CH); 3.03 (m, 2H, CH$_2$); 3.63 (s, 2H, CH$_2$); 5.28 (s, 2H, CH$_2$); 6.79 (d, 1H, J=8.2 Hz, aromatic H); 6.95 (br, s, 1H, aromatic H); 7.10 (d, 1H, J=8.2 Hz, aromatic H); 7.15 (m, 2H, aromatic H); 7.56 (m, 2H, aromatic H); 7.88 (br. s, 1H, aromatic H); 8.53 (s, 1H, aromatic H); 8.71 (s, 1H, aromatic H); 8.95 (s, 1H, aromatic H); $^{13}$C NMR (125.7 MHz, CDCl$_3$) δ=33.29 (CH$_2$), 40.81 (CH$_2$), 41.67 (CH), 54.05 (CH$_2$), 60.19 (CH$_2$), 68.73 (CH$_2$), 114.05 (aromatic-C), 115.90 (aromatic-C), 116.09 (aromatic-C), 117.83 (aromatic-C), 122.36 (aromatic-C), 127.42 (aromatic-C), 128.80 (aromatic-C), 133.71 (aromatic-C), 135.00 (aromatic-C), 135.47 (aromatic-C), 141.34 (aromatic-C), 146.94 (aromatic-C), 148.90 (aromatic-C), 153.47 (C=O), 161.90 (aromatic-C), 163.86 (aromatic-C). Calculated (%) for $C_{25}H_{25}FN_4O$ (416.20); C: 72.09, H: 6.05, N: 13.45. found (%); C: 72.01, H: 6.11, N: 13.36.

Example 29

Synthesis of 7-(1-(3-cyclopentenylbenzyl)piperidin-4-yl)-3,4-dihydroquinazolin-2(1H)-one 6e Following the same procedure adopted for the synthesis of 5a, the reductive amination of compound 6 with the aldehyde of e afforded 0.082 g (50%) of compound 6e as an off-white semi solid. IR (KBr) vmax. cm$^{-1}$: 3438, 3176 (NH), 3056 (Ar—H), 2955 (Alph-H), 1690 (C=O), 1623, 1516, 1413 (C=C), 1170 (C—O). $^1$H NMR (500 MHz, CDCl$_3$) δ=1.80-1.87 (m, 4H, 2CH$_2$); 2.00-2.03 (m, 2H, CH$_2$); 2.09 (m, 2H, CH$_2$); 2.48-2.52 (m, 3H, CH, CH$_2$); 2.71 (m, 2H, CH$_2$); 3.16 (m, 2H, CH$_2$); 3.69 (s, 2H, CH$_2$); 5.25 (s, 2H, CH$_2$); 6.20 (br. s, 1H, CH); 6.82 (d, 1H, J=8.3 Hz, aromatic H); 6.94 (s, 1H, aromatic H); 7.08 (d, 1H, J=8.3 Hz, aromatic H); 7.23-7.45 (m, 4H, aromatic H); 9.12 (br. s, 1H, NH); $^{13}$C NMR (125.7 MHz, CDCl$_3$) δ=23.24 (CH$_2$), 32.61 (CH$_2$), 33.11 (CH$_2$), 33.24 (CH$_2$), 41.41 (CH), 53.49 (CH$_2$), 62.65 (CH$_2$), 68.63 (CH$_2$), 114.20 (aromatic-C), 117.85 (aromatic-C), 122.31 (aromatic-C), 124.82 (aromatic-C), 126.49 (aromatic-C) 126.82 (aromatic-C), 127.48 (aromatic-C), 128.14 (aromatic-C), 128.24 (aromatic-C), 133.91 (aromatic-C), 136.87 (aromatic-C), 140.87 (aromatic-C), 142.09 (aromatic-C), 153.46 (C=O). Calculated (%) for $C_{25}H_{29}N_3O$ (387.23); C: 77.48, H: 7.54, N: 10.84. found (%); C: 77.40, H: 7.60, N: 10.77.

Example 30

Synthesis of 7-(1-((5-cyclopentenylpyridin-3-yl)methyl)piperidin-4-yl)-3,4-dihydroquinazolin-2(1H)-one 6f Following the same procedure adopted for the synthesis of 5a, the reductive amination of compound 6 with the aldehyde of f afforded 0.088 g (51%) of compound 6f as a light brown solid, m.p. 166-167° C.; IR (KBr) vmax. cm$^{-1}$: 3428, 3170 (NH), 3066 (Ar—H), 2953 (Alph-H), 1692 (C=O), 1606, 1515, 1416 (C=C), 1172 (C—O). $^1$H NMR (500 MHz, CDCl$_3$) δ=1.80-1.91 (m, 4H, 2CH$_2$); 2.02-2.04 (m, 2H, CH$_2$); 2.28 (m, 2H, CH$_2$); 2.54 (m, 3H, CH, CH$_2$); 2.73 (m, 2H, CH$_2$); 3.13 (m, 2H, CH$_2$); 3.72 (s, 2H, CH$_2$); 5.27 (s, 2H, CH$_2$); 6.34 (br. s, 1H, CH); 6.34 (br. s, 1H, CH); 6.82 (d, 1H, J=8.3 Hz, aromatic H); 6.96 (s, 1H, aromatic H); 7.09 (d, 1H, J=8.3 Hz, aromatic H); 7.89 (s, 1H, aromatic H); 8.40 (s, 1H, aromatic H), 8.61 (s, 1H, aromatic H), 9.05 (s, 1H, NH); $^{13}$C NMR (125.7 MHz, CDCl$_3$) δ=23.14 (CH$_2$), 32.54 (CH$_2$), 32.86 (CH$_2$), 33.39 (CH$_2$), 41.31 (CH), 53.69 (CH$_2$), 59.81, (CH$_2$), 68.66 (CH$_2$), 114.21 (aromatic-C), 117.94 (aromatic-C), 122.38 (aromatic-C), 127.53 (aromatic-C), 128.96 (aromatic-C), 132.30 (aromatic-C), 134.01 (aromatic-C), 139.10 (aromatic-C), 140.65 (aromatic-C), 146.36 (aromatic-C), 148.47 (aromatic-C), 153.41 (C=O). Calculated (%) for $C_{24}H_{28}N_4O$ (388.23); C: 74.20, H: 7.26, N: 14.42. found (%); C: 74.13, H: 7.33, N: 14.33.

It is to be understood that the present invention is not limited to the embodiments described above, but encompasses any and all embodiments within the scope of the following claims.

I claim:
1. A dihydroquinone derivative of piperidine and piperazine, comprising a compound of the formula:

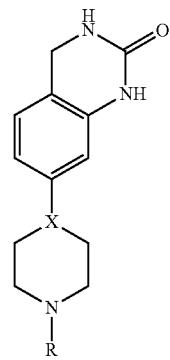

wherein X is nitrogen and R is a group selected from a, b, c, d, e, and f having the formula:

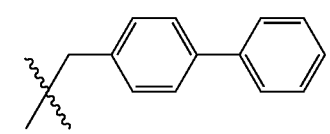
a

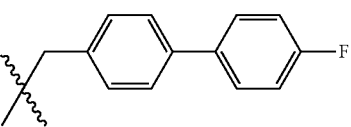
b

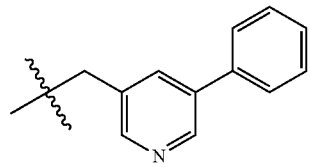
c

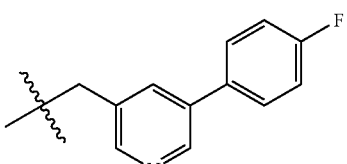
d

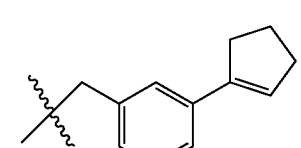
e

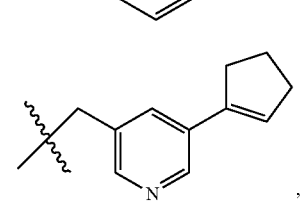
f or a pharmaceutically acceptable salt thereof.

2. The dihydroquinone derivative of piperidine and piperazine according to claim 1, wherein R is group a.

3. The dihydroquinone derivative of piperidine and piperazine according to claim 1, wherein R is group b.

4. The dihydroquinone derivative of piperidine and piperazine according to claim 1, wherein R is group c.

5. The dihydroquinone derivative of piperidine and piperazine according to claim 1, wherein R is group d.

6. The dihydroquinone derivative of piperidine and piperazine according to claim 1, wherein R is group e.

7. The dihydroquinone derivative of piperidine and piperazine according to claim 1, wherein R is group f.

8. A method of making a dihydroquinone derivative of piperazine, comprising the steps of:
    condensing 4-bromo-2-nitro-benzonitrile with 1-Boc-piperazine (1-tert-butoxycarbonyl-piperazine) to form an intermediate;
    converting the intermediate to a piperazinyl-3,4-dihydroquinazolin-2(1H)-one; and
    reductively aminating the piperazinyl-3,4-dihydroquinazolin-2(1H)-one with a biarylaldehyde having a functional group selected from group a, b, c, d, e, and f having the formulas:

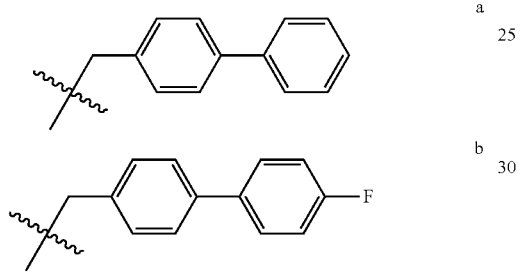

a b

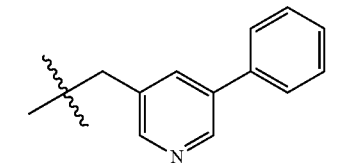

c

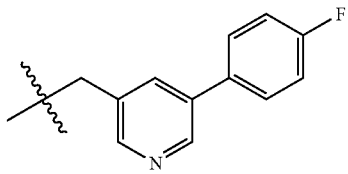

d

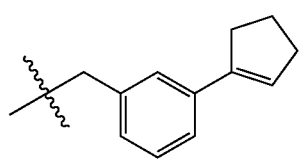

e

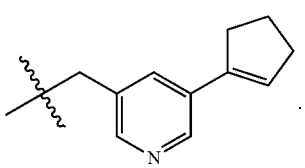

f

* * * * *